US00PP12471P2

(12) United States Plant Patent
Olesen et al.

(10) Patent No.: US PP12,471 P2
(45) Date of Patent: Mar. 19, 2002

(54) SHRUB ROSE PLANT NAMED 'POULALO'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/268,301

(22) Filed: Mar. 16, 1999

(51) Int. Cl.[7] ..... A01H 5/00

(52) U.S. Cl. ..... Plt./107

(58) Field of Search ..... Plt./102, 107, 108

(56) References Cited

PUBLICATIONS

Certificate on the Grant of Community Plant Variety Rights, EO3597, Oct. 5, 1998.*

Application for Community Plant Variety Right for QZ PBR 970137, 'POULalo'.*

UPOV–ROM, 2000/04, Plant Variety Database, GTI Jouve Retrieval Software, 2 citations for 'POULalo'.*

* cited by examiner

*Primary Examiner*—Howard J. Locker

(57) ABSTRACT

A new garden rose plant which has abundant, double, coral pink flowers and attractive, disease resistant foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing in the summer of 1990 between an unnamed seedling and Bonica 82. The resulting seeds were planted in a controlled environment. The new variety is named 'POULalo'. The new rose may be distinguished from its seed parent, an unnamed seedling, characteristics:

1. The unnamed seed parent is a ground cover rose with bushy and spreading growth, whereas 'POULalo' is a tall, bushy shrub with slightly arching canes; and 2. The unnamed seed parent has pink semi-double flowers, while 'POULalo' has coral pink double flowers in large clusters.

The new variety may be distinguished from its pollen parent, Bonica 82 created by the same inventors, by the following combination of characteristics:

1. The pollen parent has soft pink flowers which are 60 mm in diameter with 35 to 40 petals while 'POULalo' has coral pink, high centered, very double flowers which are 55–60 mm in diameter with 60–70 petals; and 2. The pollen parent is bushy and somewhat compact, while 'POULalo' is a tall, bushy shrub with slightly arching canes.

The objective of the hybridization of this rose variety for nursery and garden use was to create a new and distinct variety with unique qualities, such as:

1. Abundant, coral pink flowers;

2. A tall growing shrub rose with uniform growth and a spreading habit;

3. Glossy and disease resistant foliage which requires limited maintenance, making it ideal for use in landscapes; and 4. Good growth on its own roots as well as a traditionally budded plant.

This combination of qualities is not present in previously available commercial cultivars of this type and distinguish 'POULalo' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULalo' was selected by the inventors in the spring of 1991 as a single plant from the progeny of the aforementioned hybridization.

Asexual reproduction of 'POULalo' by traditional budding was first done by L. Pernille and Mogens N. Olesen in August 1991, at their nursery in Fredensborg, Denmark. Other subsequent propagations conducted in controlled environments have demonstrated that the characteristics of 'POULalo' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULalo'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULalo', as observed in its outdoor growth in a field nursery in Jackson County, Oreg. Observations were conducted during August 1991, using The Royal Horticultural Society (London, England) Colour Chart, 1995, except where common terms of color are used. For a comparison, several physical characteristics of the rose variety 'POULfan', a rose variety from the same inventors described and illustrated in U.S. Plant Pat. No. 9,641 and issued on 10 Sep. 1996 are compared to 'POULalo' in Chart 1.

CHART 1

| | 'POULalo' | 'POULfan' |
|---|---|---|
| Petalage of flower bloom. | Average range 60–70 petals under normal conditions. | Approximately 5 petals under normal conditions. |
| Flower petal color, upon opening, upper surface. | Red-Purple Group 58C–58D. | Red Group 49A. |
| Flower petal color, open flower, upper surface. | Red-Purple Group 55A–55B. | Red Group 56C. |

Parents:

*Seed parent.*—Unnamed, unpatented seedling.

*Pollen parent.*—Bonica 82.

Classification:

*Botanical.*—*Rosa hybrida.*

*Commercial.*—Shrub.

FLOWER AND FLOWER BUD

Blooming habit: Recurrent.

Flower bud:

*Size.*—Upon opening, 18–24 mm in length from base of receptacle to end of bud.

*Bud form.*—Pointed-ovoid to globular.

*Bud color.*—As sepals unfold, Red Group 47A–48B. Red Group 48B at ¼ opening.

*Sepals.*—Yellow-Green Group 146C. Weak foliaceous appendages on three of the five sepals. Surfaces of sepals slightly pubescent. Stipitate glands are present in limited numbers on margins.

*Receptacle.*—Surface: Smooth. Some with a few fine, white hairs. Shape: Funnel shaped. Size: Small 0.5 mm (h)×5 mm (w). Color: Yellow-Green Group 144B.

*Peduncle.*—Surface: Smooth. Few to no stipitate glands. Length: 25–30 mm average length. Color: Yellow-Green Group 144B, but generally Greyed-Red Group 181A. Strength: Upright.

*Borne.*—Multiple buds per stem. Generally with 12–25 blooms per flowering stem.

Flower bloom:

*Fragrance.*—None.

*Duration.*—Variety not tested as a cut flower. The blooms have a duration on the plant of approximately 3 to 4 days, after which petals drop cleanly.

*Size.*—Average flower diameter is 55–60 mm when open.

*Form.*—Shape of flower when viewed from the side: Upon opening, upper part: Flattened convex. Upon opening, lower part: Flattened convex. Open flower, upper part: Flattened convex. Open flower, lower part: Concave.

*Petalage.*—Very double. Average range: 60–70 petals under normal conditions with 5–10 petaloids.

Color:

*Upon opening, petals.*—Outermost petals: Upper Surface: Red-Purple Group 58C–58D. Reverse Side: Red-Purple Group 58C. Innermost petals: Upper Surface: Red-Purple Group 58B–58C. Reverse Side: Red-Purple Group 58B.

*Upon opening, basal petal spots.*—Outermost petals: Outer Side: Yellow Group 2C–D. Inner Side: Yellow Group 2C–D. Innermost petals: Outer Side: Yellow Group 1C. Inner Side: Yellow Group 1C.

*After opening, petals.*—Outermost petals: Upper Surface: Red Group 55B–55A. Reverse Side: Red-Purple Group 58C–58D. Innermost petals: Upper Surface: Red-Purple 58C–58D. Reverse Side: Red-Purple 58C.

*Upon opening, basal petal spots.*—Petals: Outer Side: Green-Yellow 1C–D. Inner Side: Green-Yellow 1C.

General tonality: On open flower, Red Purple Group 58C–58D. No change in the general tonality at the end of the third day. Afterwards, general tonality is Red-Purple Group 55B–55C.

Petals:

*Petal reflex.*—All petals except innermost are reflexed, outermost double reflexed.

*Petal edge.*—Uniform.

*Shape.*—Deltoid shaped.

*Petaloids.*—Present. Quantity: 5–10.

*Thickness.*—Average.

*Arrangement.*—Imbricated.

Reproductive organs:

*Pollen.*—Color: Yellow Group 13C. Abundance: Limited abundance.

*Anthers.*—Size: Small. Color: Immature: Greyed-Orange Group 166C to Greyed-Purple Group 184C. Mature: Brown 200C. Abundance: Limited.

*Filaments.*—Color: Grey-Orange Group 163B.

*Stigmas.*—When present, stigmas superior in location to anthers. Color: When present, Yellow-Green Group 145D.

*Styles.*—Color: Green-White Group 157A.

*Other intonations.*—Below stigmas, Red-Purple Group 57C.

*Hips.*—None observed.

PLANT

Plant growth: Vigorous and bushy with slightly arching canes. When grown as a budded field grown plant on *Rosa multiflora* understock, the average height of the plant itself is 100 cm and the average width is 90 cm.

Stems:

*Color.*—Young wood: Green Group 144A. Older wood: Yellow-Green Group 144B.

*Thorns.*—Incidence: 3 to 5 thorns per 10 cm of stem. Size: Average length: 5–6 mm. Color, young: Greyed-Orange Group 180C. Color, Older: Greyed-Orange Group 168D. Shape: Downwardly hooked; concave on lower side.

*Surface.*—Young wood: Smooth. Older wood: Smooth.

Plant foliage: Normal number of leaflets on normal leaves in middle of the stem: 5 leaflets.

*Leaf size.*—Small. 85–95 mm (l)×55–65 mm (w).

*Abundance.*—Average abundance.

*Color.*—Upper Leaf Surface: Green Group 137A. Lower Leaf Surface: Yellow-Green Group 146C–146D. Juvenile foliage: Upper surface: Green Group 137A Lower surface: Green Group 137A. Anthocyanin intonation: Yes. Location: Leaflet margins and lower leaflet surface of juvenile foliage; petiole, and rachis of juvenile foliage. Color: Greyed-Purple Group 187C.

Plant leaves and leaflets:

*Stipules.*—Size: 12 mm–14 mm. Color: Green Group 143A–144A. Presence of stipitate glands: Limited numbers on margins.

*Petiole.*—Length: 20mm–25 mm. Color: Green Group 137A–137B. Underneath: Smooth, Glabrous. Margins: Smooth.

*Rachis.*—Color: Green Group 137A–137B. Underneath: Smooth. Margins: With limited stipitate glands.

*Leaflet.*—Edge: Serrated. Shape: Ovate.

*Other.*—Moderately glossy to glossy. Average to thick texture.

Disease resistance: Above average resistance to mildew, Black spot, and Botrytis under normal growing conditions in Jackson County, Oreg.

Winter hardiness: Winter hardy in Denmark and in Jackson County, Oreg.

We claim:

1. A new and distinct variety of rose plant of the shrub class, substantially as herein illustrated and described as a distinct and novel rose variety due to its abundant, coral pink flowers, vigorous but uniform growth, and exceptional disease resistance.

* * * * *

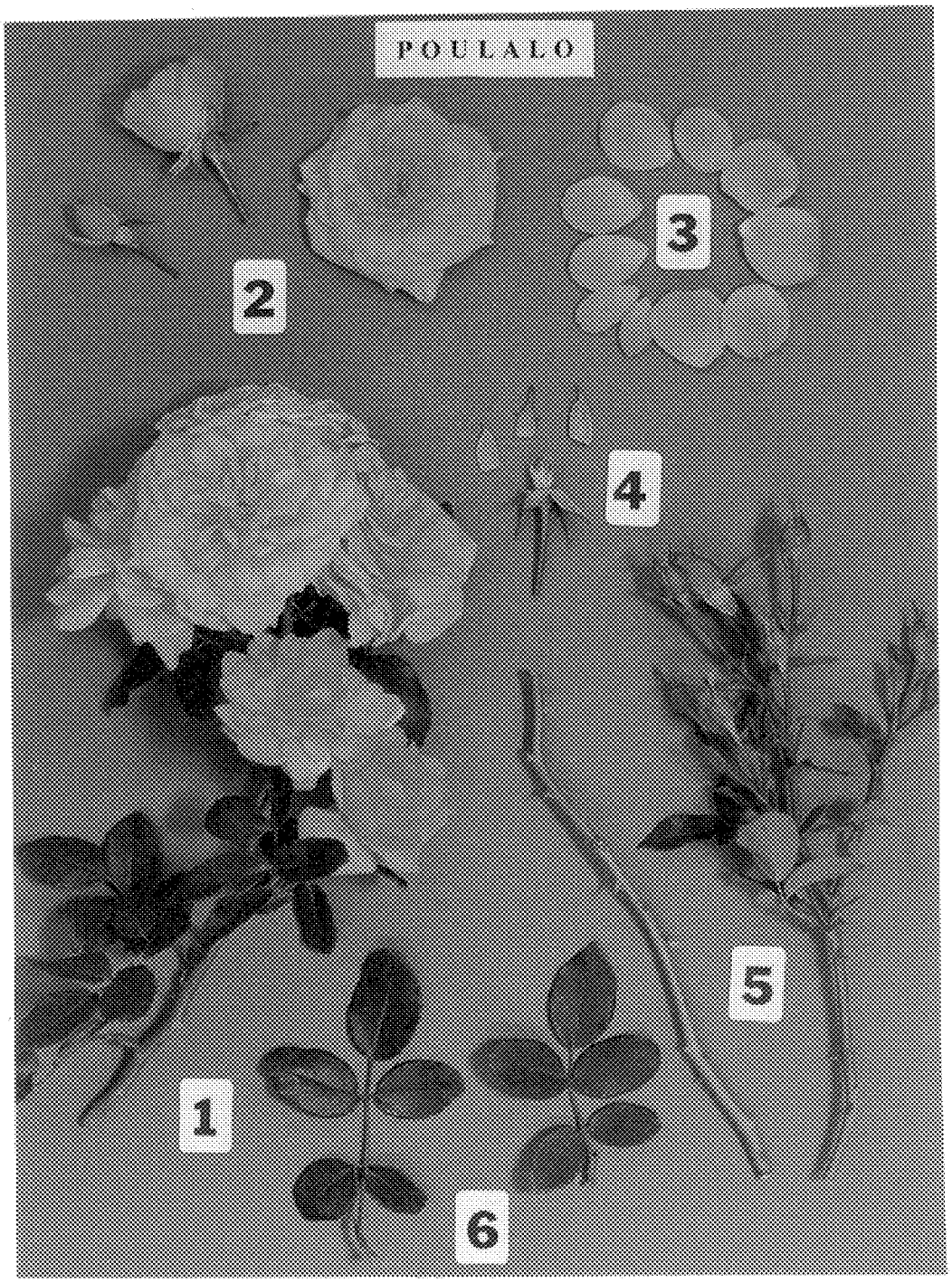
POULALO
1
2
3
4
5
6